US00PP33508P2

(12) United States Plant Patent
Fouillet

(10) Patent No.: US PP33,508 P2
(45) Date of Patent: Sep. 28, 2021

(54) APPLE TREE NAMED 'R202'

(50) Latin Name: *Malus domestica*
Varietal Denomination: R202

(71) Applicant: IFO S.A.R.L., Seiches sur le Loir (FR)

(72) Inventor: Valérie Fouillet, Saint Sylvain d'Anjou (FR)

(73) Assignee: IFO S.A.R.L., Seiches sur le Loir (FR)

( * ) Notice: Subject to any disclaimer, the term of this patent is extended or adjusted under 35 U.S.C. 154(b) by 0 days.

(21) Appl. No.: 16/602,716

(22) Filed: Nov. 25, 2019

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418
See application file for complete search history.

*Primary Examiner* — Anne Marie Grunberg
(74) *Attorney, Agent, or Firm* — Michelle Bos Legal LLC

(57) ABSTRACT

'R202' apple tree is a new variety selected for its distinctive and flavorful red-and-white fleshed fruit, which is well-suited for the fresh market.

8 Drawing Sheets

Latin name: *Malus domestica.*
Variety denomination: 'R202'.

BACKGROUND OF THE VARIETY

'R202' is a new and distinct variety of apple tree (*Malus domestica*) obtained from a controlled cross of 'Dalitron' (female parent, U.S. Plant Pat. No 16,753) x 'HY63-2' (male parent, not patented) carried out at Seiches sur le Loir, France in 2005. Seeds obtained from the cross were planted at Seiches sur le Loir, and 'R202' was selected from the resulting seedlings for propagation and further observation. 'R202' was first asexually propagated by grafting at Seiches sur le Loir in 2013, and has since been observed to remain true to type over successive asexually propagated generations.

BRIEF DESCRIPTION OF THE VARIETY

'R202' apple tree is distinguished by its sweet red-fleshed fruit. Comparisons of 'R202' to its parents and to similar variety 'R201' (U.S. Plant Pat. No. 28,218) are shown in Tables 1, 2 and 3 below.

TABLE 1

Comparison of 'R202' to Female Parent 'Dalitron'

| Characteristic | 'R202' | 'Dalitron' |
|---|---|---|
| Flesh Color | Red 48C and White 155D | White 155D |
| Skin Color | Red 53A and Red 45A | Green-yellow 150C |
| Flavor | More sweet | Less sweet |
| Harvest Date | 1 week before 'Dalitron' | 1 week after 'R202' |

TABLE 2

Comparison of 'R202' to Male Parent 'HY63-2'

| Characteristic | 'R202' | 'HY63-2' |
|---|---|---|
| Aroma | More aromatic | Less aromatic |
| Russeting on Fruit Skin | Less russeting | More russeting |
| Flesh Color Intensity | Less intense | More intense |
| Flavor Comparison | Less acidic, more sweet | More acidic, less sweet |

TABLE 3

Comparison of 'R202' to Similar Variety 'R201'

| Characteristic | 'R202' | 'R201' |
|---|---|---|
| Fruit Size | Larger: 84 mm diameter, 76 mm height | Smaller: 78 mm diameter, 67 mm height |
| Russet on Fruit Skin | Much less russet | More russet |
| Juiciness | Very high | Moderate |
| Tree Habit | Spreading | Drooping |
| Harvest date | Earlier, similar to 'Red Delicious'* | Later, similar to 'Braeburn'* |

*not patented

BRIEF DESCRIPTION OF THE PHOTOGRAPHS

DETAILED BOTANICAL DESCRIPTION OF THE VARIETY

Figure 1:
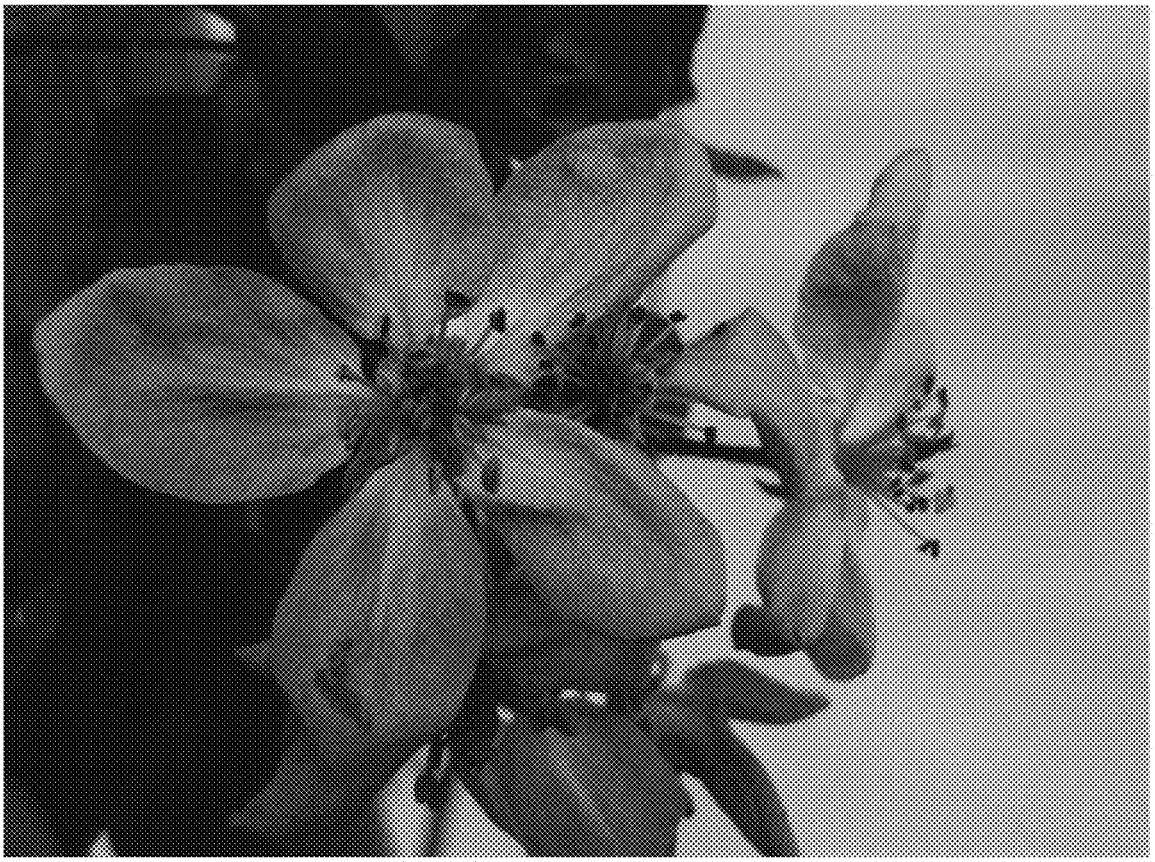
FIG. 1 is a photograph of a flower of an 'R202' apple tree.
Figure 2:
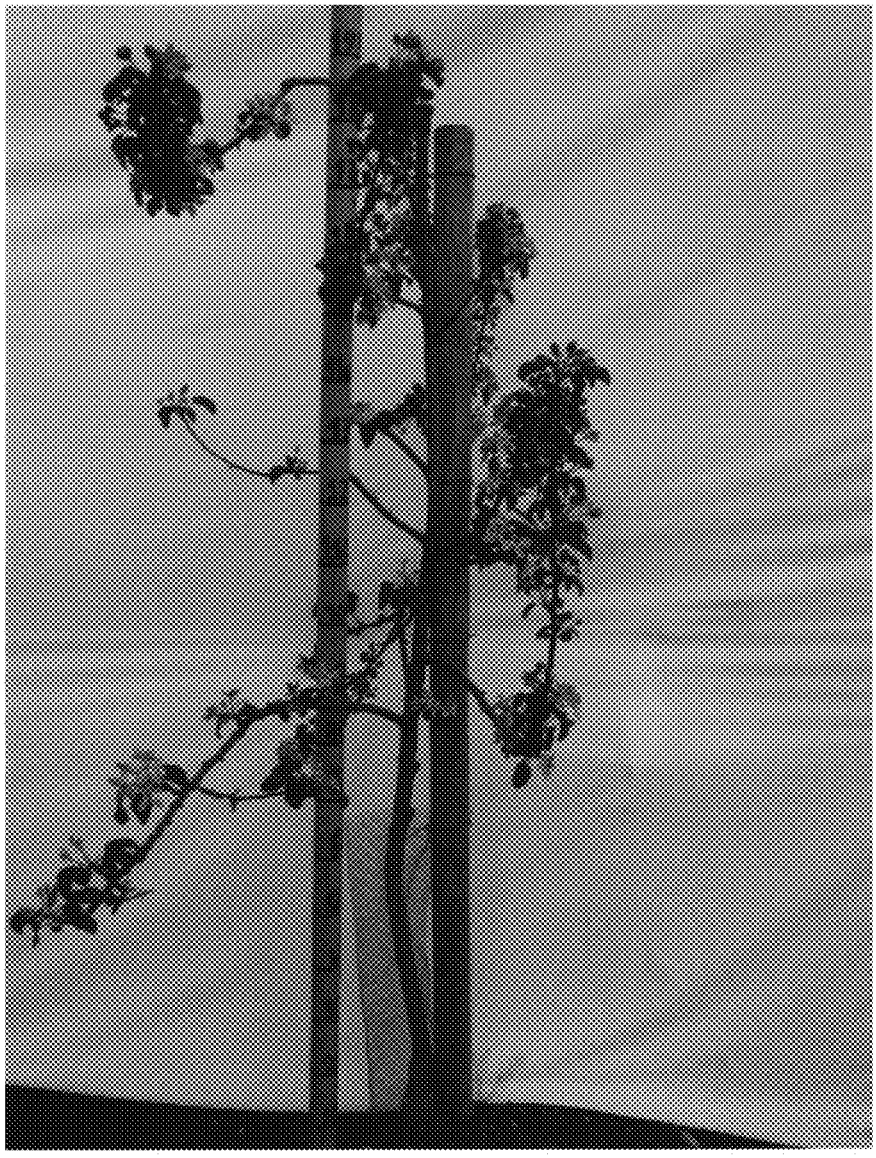
FIG. 2 is a photograph of an 'R202' apple tree with young leaves and flowers.
Figure 3:
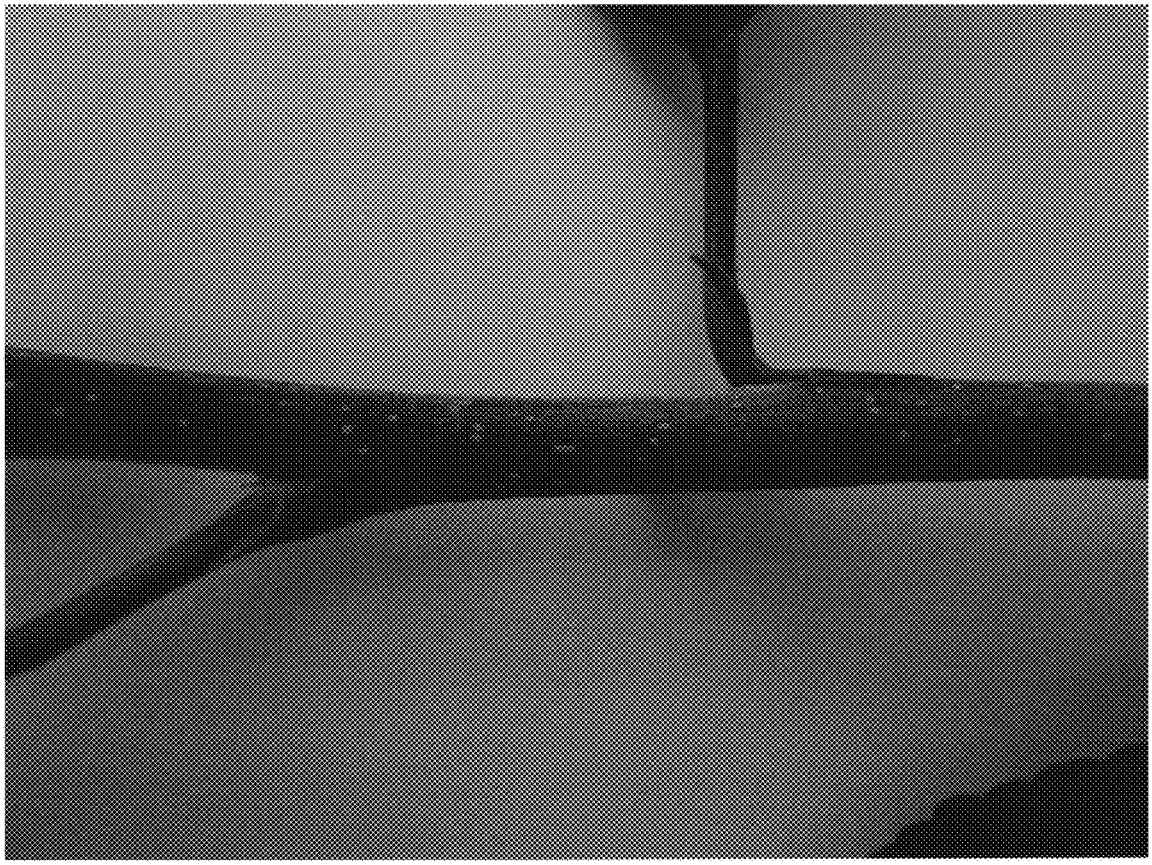
FIG. 3 is a photograph of a one year old shoot of an 'R202' apple tree.
Figure 4:
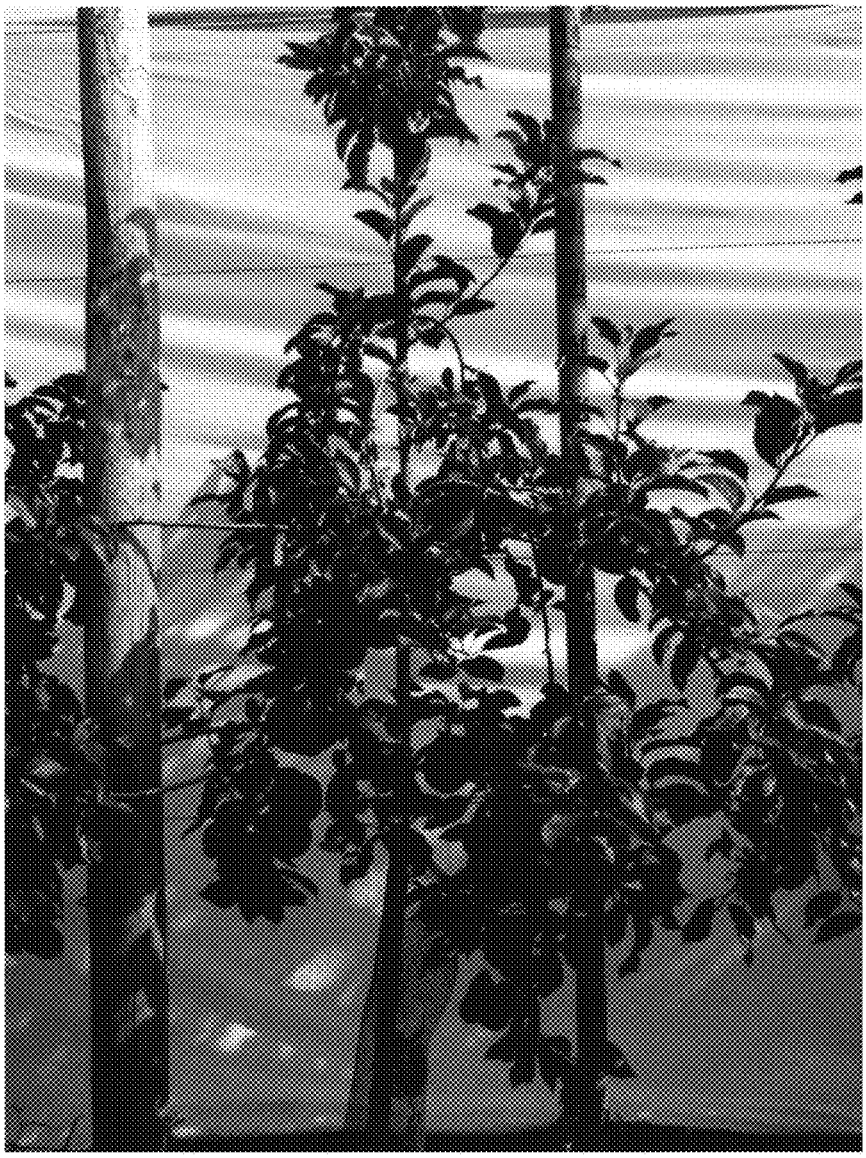
FIG. 4 is a photograph of an 'R202' apple tree with mature leaves.
Figure 5:
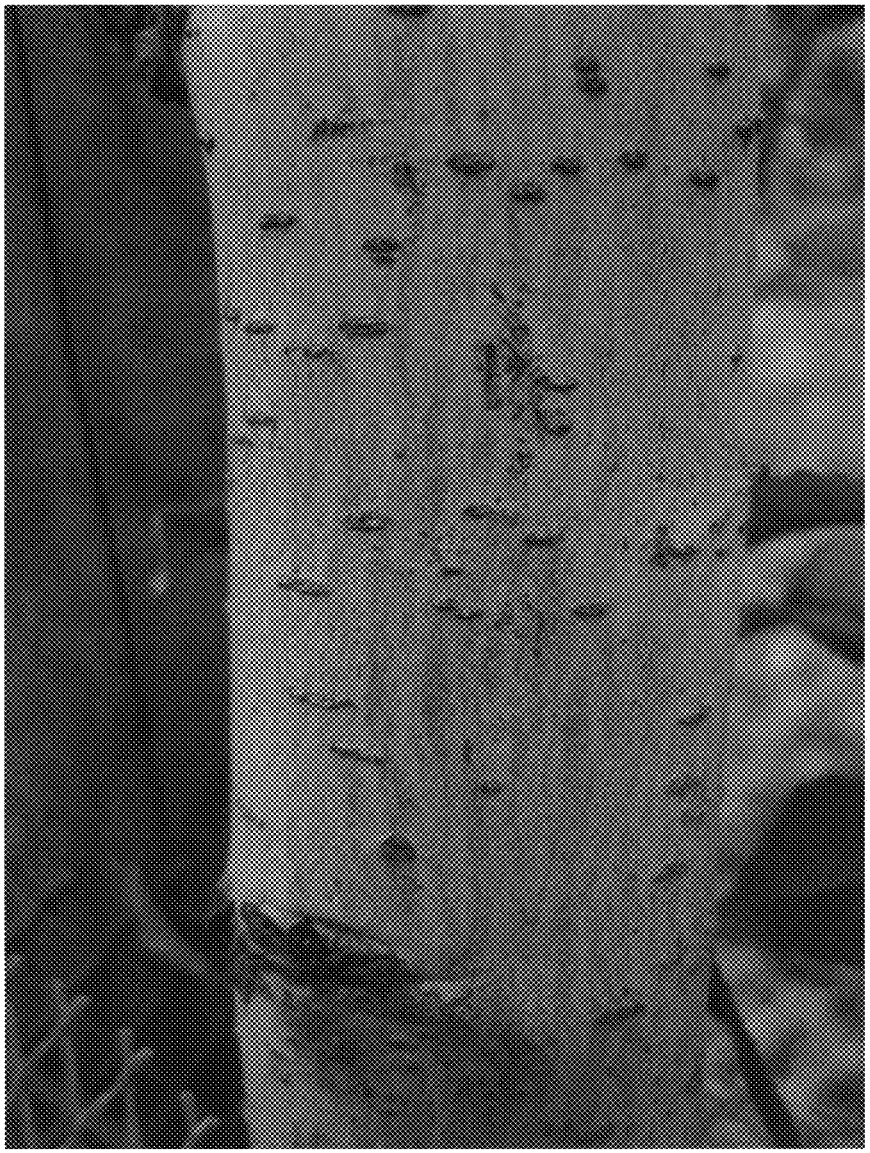
FIG. 5 is a photograph of the trunk of an 'R202' apple tree.
Figure 6:
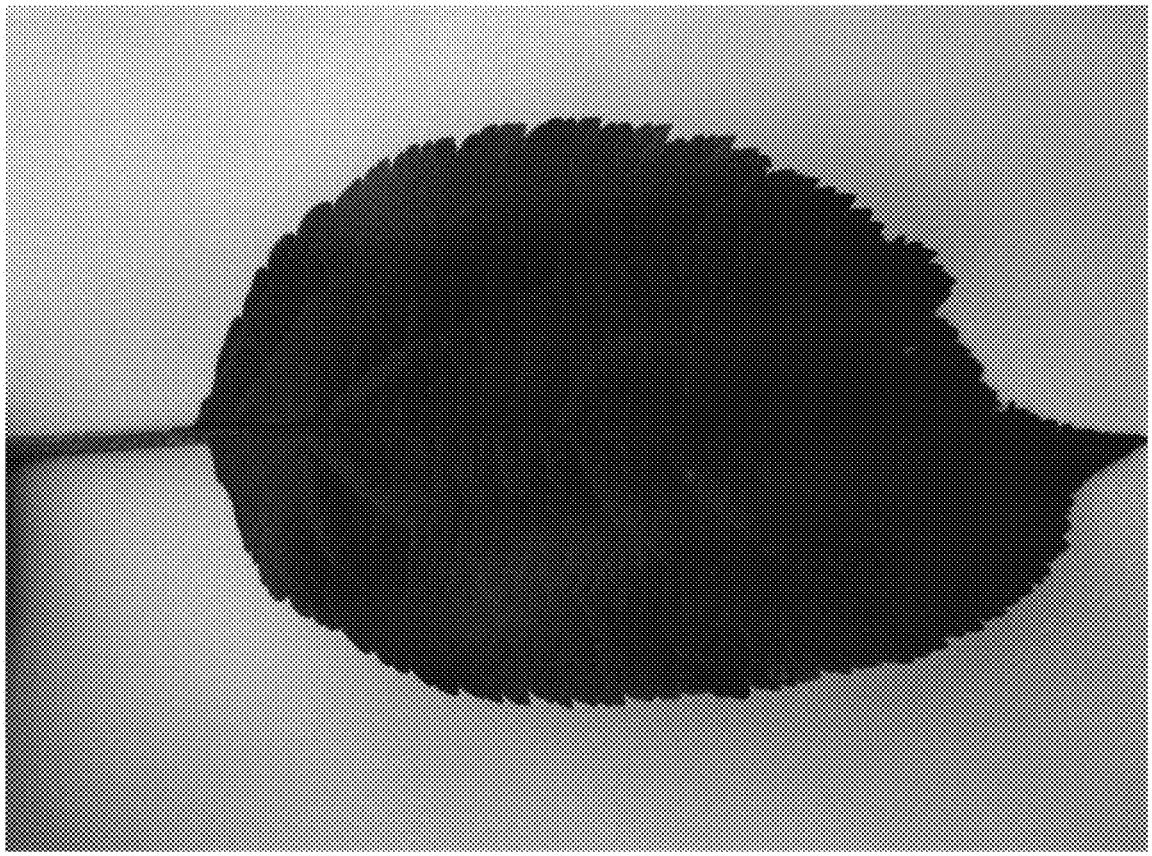
FIG. 6 is a photograph of the upper surface of a leaf of an 'R202' apple tree.
Figure 7:
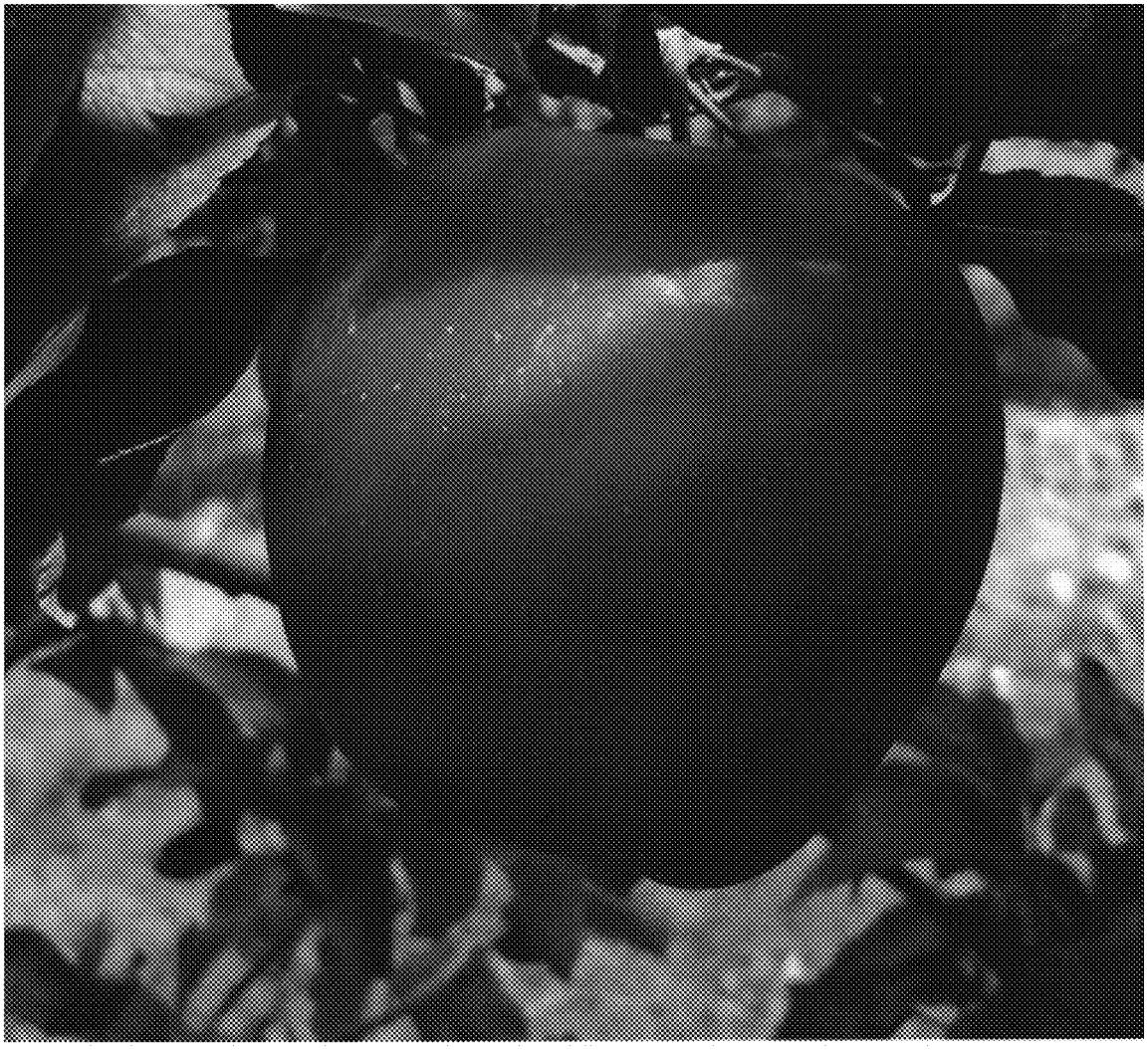
FIG. 7 is a photograph of a fruit on an 'R202' apple tree.

The accompanying photographs and the following detailed botanical description were obtained at Seiches sur le Loir, France during 2016 and 2017, of trees planted in 2013 and grown on Pajam®2 'Cepiland' (U.S. Plant Pat. No. 7,715) rootstock. All colors are described according to The Royal Horticultural Society Mini Colour Chart (2005). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor*.—Moderate.
- *Type*.—Ramified.
- *Habit*.—Spreading.
- *Spread of mature tree*.—1.4 meters.
- *Height*.—Approximately 2.3 m.
- *Trunk diameter* (*at* 30 *cm above the graft*).—34 mm.
- *Bearing*.—On shoots.
- *Bark texture*.—Smooth.
- *Bark color*.—Brown N200C.
- *Lenticel length*.—2.5 mm.
- *Lenticel width*.—0.8 mm.
- *Lenticel height*.—0.4 mm.
- *Lenticel shape*.—Oblong.
- *Lenticel color*.—Greyed orange N170A.

Branch (fruiting branches located at around 1 m above the graft union):
- *Length*.—1 m.
- *Diameter*.—12 mm.
- *Crotch angle*.—80°.
- *Bark color*.—Brown N200C.
- *Lenticel length*.—2.3 mm.
- *Lenticel width*.—0.8 mm.
- *Lenticel height*.—0.4 mm.
- *Lenticel shape*.—Round to oblong.
- *Lenticel color*.—Greyed orange 163A.
- *Number of lenticels per cm*$^2$.—3.

One year old shoot:
- *Length*.—42 cm.
- *Diameter*.—6 mm.
- *Growth pattern*.—Straight.
- *Color*.—Greyed purple 183A.
- *Pubescence*.—Moderately pubescent.
- *Internode length*.—32 mm.
- *Lenticel length*.—0.8 mm.
- *Lenticel width*.—0.8 mm.
- *Lenticel height*.—0.3 mm.
- *Lenticel shape*.—Round.
- *Lenticel color*.—Greyed yellow 160B.
- *Number of lenticels per cm*$^2$.—6.
- *Position of vegetative buds in relation to shoots*.—Stipitate, semi-erect to horizontal.
- *Shape of vegetative bud apex*.—Acute.
- *Color of vegetative bud*.—Greyed purple 187A.

Flower buds:
- *Quantity per spur*.—5.
- *Bud shape*.—Conical.
- *Apex shape*.—Rounded.
- *Length*.—11 mm.
- *Diameter*.—9 mm.
- *Color*.—Purple N79C.

Flowers:
- *Inflorescence type*.—Umbel.
- *Diameter of fully open flower*.—36 mm.
- *Flower depth*.—12.4.
- *Relative position of petal margin*.—Touching.
- *Number per cluster*.—5 to 6.
- *Fragrance*.—Moderately fragrant.
- *Date of first bloom*.—April 5 (2017 growing season); same as 'Gala'.
- *Date of full bloom*.—April 10 (2017 growing season); same as 'Gala'.
- *Pollination requirement*.—'Gala', 'Granny Smith', and 'Golden Delicious' are suitable pollinators.

Petals:
- *Number per flower*.—5.
- *Shape*.—Elliptical.
- *Length*.—19 mm.
- *Width*.—13 mm.
- *Apex*.—Obtuse.
- *Base*.—Acute.
- *Margin*.—Smooth.
- *Texture*.—Rugulose.
- *Color*.—Upper surface red purple 67A, veins red purple 61A. Lower surface red purple N74C and white N155B.

Pistils:
- *Length*.—10 mm.
- *Quantity*.—5.
- *Color*.—Red 56A and red purple 64D.

Stigma:
- *Length*.—1 mm.
- *Color*.—Red 56A.
- *Position relative to anther*.—Same level.

Style:
- *Length*.—5 mm.
- *Color*.—Red purple 64D.

Ovary:
- *Length*.—4 mm.
- *Diameter*.—2.8 mm.
- *Color*.—Green 137A.

Anthers:
- *Quantity*.—20.
- *Length*.—2 mm.
- *Diameter*.—1.2 mm.
- *Color of anther*.—Red purple 58A.
- *Pollen quantity*.—Present, neither scarce nor especially abundant.
- *Color of pollen*.—Yellow 8C.

Pedicel:
- *Length*.—25 mm.
- *Diameter*.—1.5 mm.
- *Color*.—Brown 200B.

Sepals:
- *Quantity*.—5.
- *Color*.—Upper surface green 138D. Lower surface greyed orange 166A.
- *Length*.—7.7 mm.

*Width.*—4 mm.
*Shape.*—Pointed.
*Apex.*—Acute.
*Margin.*—Smooth.
*Pubescence.*—Highly pubescent.

Leaves:
*Shape.*—Elliptical.
*Length.*—85 mm.
*Width.*—52 mm.
*Length/width ratio.*—1.63.
*Blade margin.*—Serrate, slight undulation.
*Apex.*—Pointed.
*Base shape.*—Obtuse.
*Profile in cross section.*—Concave.
*Leaf color.*—Upper surface green 137A, veins red purple 71A. Lower surface green 137C, veins red purple 71A.
*Stipule size.*—2 mm×6 mm.
*Stipule color.*—Green 137A with red purple 71A at base.
*Attitude in relation to shoot.*—Outward.

Petiole:
*Length.*—27 mm.
*Diameter.*—2 mm.
*Color.*—Red purple 71A.

Figure 8:
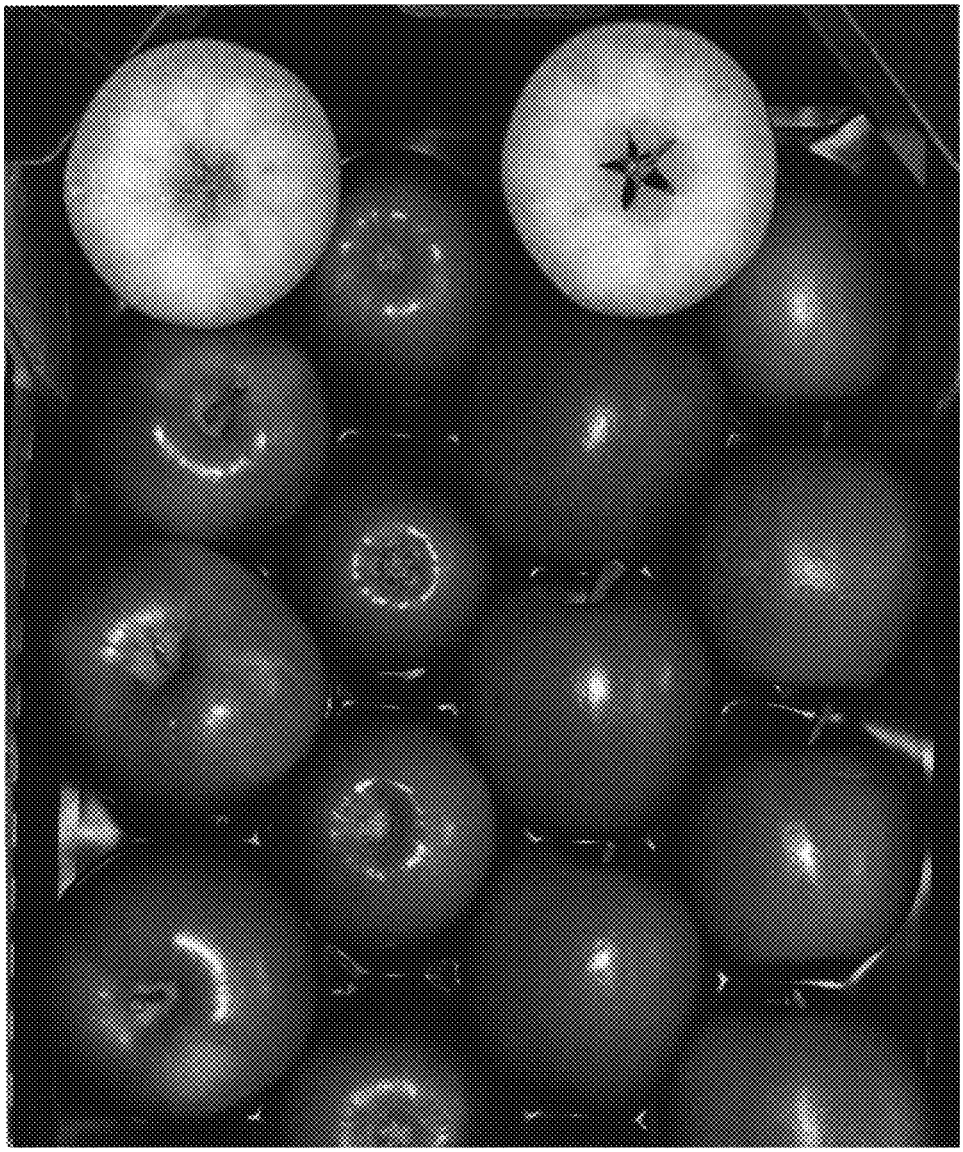
FIG. 8 is a photograph of whole and sectioned fruit from an 'R202' apple tree.

Fruit:
*Quantity per cluster.*—1 to 3.
*Diameter.*—84 mm.
*Height.*—76 mm.
*Height to width.*—0.9.
*Weight.*—279 g.
*General shape in profile.*—Globose.
*Position of maximum diameter.*—At equator.
*Ribbing.*—Not present.
*Crowning at calyx end.*—Slight.
*Bloom of skin.*—Absent or weak.
*Greasiness of skin.*—Absent or weak.
*Lenticel color.*—Yellow white 158D.
*Lenticel density.*—5 to 7 per $cm^2$.
*Lenticel shape.*—Round.
*Lenticel size.*—Diameter 0.6 mm.
*Background color of skin.*—Greyed orange 171A.
*Over color of skin.*—Red 53A and red 45A.
*Amount of over color.*—High, 95% to 100%.
*Intensity of over color.*—Moderate to high.
*Pattern of over color.*—Solid flush.
*Amount of russet around stalk cavity.*—Weak to moderate.
*Amount of russet on cheeks.*—Absent or weak.
*Area of russet around eye basin.*—Absent or weak.
*Length of stalk.*—Short, 19 mm.
*Diameter of stalk.*—Thick, 4 mm.
*Depth of stalk cavity.*—13 mm.
*Width of stalk cavity.*—37 mm.
*Depth of eye basin.*—10 mm.
*Width of eye basin.*—26 mm.
*Size of eye.*—Medium, 6.6 mm.
*Aperture of eye.*—Closed.
*Length of sepal.*—7 mm.
*Firmness of flesh.*—Medium to weak (soft but crunchy).
*Flesh texture.*—Fine.
*Aperture of locules.*—Nearly fully open.
*Aroma, flavor.*—Balanced acid-to-sugar ratio, slight berry flavor.
*Juiciness.*—Very high.
*Brix.*—11° Brix to 15° Brix.
*Flesh color.*—About 50% red 48C, primarily around the core and near the surface, and 50% white 155D (see FIG. 8).
*Stem color.*—Brown 200C.

Seeds:
*Quantity per fruit.*—8 to 12.
*Length.*—9 mm.
*Shape.*—Oval.
*Color.*—Greyed orange 170A and greyed orange 165A.

Harvest:
*Harvest date.*—September 14 (2017) similar to 'Red Delicious'.
*Number of picks.*—1 to 3.
*Fruit load per tree.*—Average 80 fruits per tree evaluated.

Disease resistance/susceptibility: None noted at the time of filing.

Storageability Medium to good; 2 months in standard cold storage.

Market use: Fresh consumption.

The invention claimed is:

1. A new and distinct apple tree substantially as described and illustrated herein.

* * * * *